United States Patent [19]
Steinbeck

[11] Patent Number: 5,649,546
[45] Date of Patent: Jul. 22, 1997

[54] METAL DETECTOR FOR THE LOCALIZATION OF A METALLIC FOREIGN BODY PENETRATED OR IMPLANTED INTO A HUMAN OR ANIMAL BODY

[76] Inventor: Ulrich Steinbeck, Nissenstrasse 13, D-20251 Hamburg, Germany

[21] Appl. No.: 175,364
[22] PCT Filed: Jun. 20, 1992
[86] PCT No.: PCT/EP92/01391
  § 371 Date: Aug. 9, 1994
  § 102(e) Date: Aug. 9, 1994
[87] PCT Pub. No.: WO93/00039
  PCT Pub. Date: Jan. 7, 1993

[30] Foreign Application Priority Data
Jun. 25, 1991 [DE] Germany ............ 91 07 798.2

[51] Int. Cl.⁶ .................................. A61B 5/06
[52] U.S. Cl. .......................... 128/737; 340/551
[58] Field of Search .................... 340/551, 500, 340/552; 128/630, 632, 634, 734, 737

[56] References Cited

U.S. PATENT DOCUMENTS

| | | |
|---|---|---|
| 4,416,289 | 11/1983 | Bresler . |
| 4,431,005 | 2/1984 | McCormick .............. 128/737 X |
| 4,445,501 | 5/1984 | Bresler .................. 128/737 X |
| 4,526,177 | 7/1985 | Rudy et al. .............. 128/737 |
| 4,905,698 | 3/1990 | Strohl, Jr. et al. ......... 128/737 X |
| 4,943,779 | 7/1990 | Ashley-Rollman et al. ...... 128/737 X |

FOREIGN PATENT DOCUMENTS

| | | |
|---|---|---|
| 0399536 | 11/1990 | European Pat. Off. . |
| 2635259 | 2/1990 | France . |
| 2130776 | 6/1984 | United Kingdom . |
| 8602539 | 5/1986 | WIPO . |
| 9000030 | 1/1990 | WIPO . |

*Primary Examiner*—Sam Rimell
*Attorney, Agent, or Firm*—Friedrich Kueffner

[57] ABSTRACT

The invention relates to a metal detecting device for the localization of a metallic foreign body penetrated or implanted into a human or animal body, comprising coil facilities (19) arranged inside a sensor pin (10) and connected with a measuring amplifier, the output signals of which, as a degree for the field influence caused by the metallic foreign body, are evaluatable by a measuring comparator, said metal detecting device allowing a three-dimensional and one-hand controlled detection of metallic foreign bodies (FIG. 1).

12 Claims, 3 Drawing Sheets

METAL DETECTOR FOR THE LOCALIZATION OF A METALLIC FOREIGN BODY PENETRATED OR IMPLANTED INTO A HUMAN OR ANIMAL BODY

BACKGROUND OF THE INVENTION

1. Field of the Invention

The present invention relates to a metal detector for localizing a foreign metal body which has penetrated or has been implanted into a human or animal body.

2. Description of the Related Art

The localization of foreign metal bodies which have penetrated or been implanted into a body frequently causes unforeseen difficulties, e.g., as a result of scarring, bony concretions or a complicated position within the body. For this reason, the localization and the extraction may involve a considerable amount of work and expenditure of time.

Foreign metal bodies are considered to be metal parts which have pentrated into the body or implanted osteosynthesis materials, such as screws, nuts, tension boom wires and cerclage wires, Kirschner's wires and also so-called fixations for epitheses. The foreign metal bodies which have penetrated in this manner must be removed in order to prevent infections or other reactions of the tissue to foreign bodies.

Any implanted foreign metal body should generally be removed after a guaranteed fracture union because the points of proximal contact with the body tissue may corrode and lead to an undesired foreign body irritation, this because the implant causes an elasticity loss of the bone.

In the case of fixations, these fixations have to be localized precisely at the recovery in order to make it possible to secure the so-called epitheses thereto.

Although, for the detection of an implant, the scar of the orignal area of operation is usually circumcised, it is frequently impossible to localize the material by feeling or by means of needles because it is either covered by a scar tissue or callus layer or it may also have moved in rare cases.

According to the prior art, a radiologic representation of the material is made, for example, by means of an X-ray image converter which is slewable through 360°. The disadvantage of this method is the fact that only the horizontal or vertical, i.e. the two-dimensional, position of the material is indicated successively. Consequently, only the position with respect to its width or depth is visible on the X-ray, even though the work is performed on a three-dimensional body.

In difficult cases, the location is usually determined by narrowing down the position of the foreign body by means of needles which are inserted into the tissue, i.e., an approach to the foreign body is carried out by more or less frequent X-ray exposures.

However, this method has the following disadvantages:

The patient and the personnel are exposed to X-ray doses which are not insignificant;

the personnel has to work under aggravated conditions since, because of the radiation exposure, it is compulsory to wear heavy lead rubber aprons;

the search for a foreign metal body causes damage to the tissue;

the removal of the metal may require a relatively large amount of time, so that the patient needs to be narcotized an equally long time, i.e. for long work periods and correspondingly long occupancy periods of operating rooms;

at least two persons are required for removal of the metal namely, an operator and an assistant for operating the X-ray C-arc.

SUMMARY OF THE INVENTION

Therefore, it is the primary object of the present invention to provide a metal detecting device of the type described above which permits a three-dimensional localization of foreign metal bodies in human or animal bodies and which allows a single-handed operation. In addition, the device should be suitable for stationary or mobile use.

In accordance with the present invention, the device of the above-described type includes a measuring coil member arranged in a sensor which is shaped like a pin, wherein the measuring coil member is connected to a corresponding amplifier, and wherein the output signals of the amplifier can be evaluated by means of a measuring comparator as a degree for the field influence caused by the foreign metal body.

The device constructed in accordance the present invention makes possible an exact, reliable and quick localization of foreign metal bodies in the tissue with respect to depth, length and width, irrespective of the type of metal. The device is especially useful for the medical-operative fields; however, the device can also be used wherever similar problems arise.

The single-handed operation which is indispensable for surgical use is ensured by a special circuit arrangement inside the sensor pin which controls the localization procedure. Due to the new construction of the completely temperature-resistant probe, the device can be sterilized easily in the autoclave under a saturated steam pressure with the usual surgical instruments. This is also true for the plug and cable connection. The hand of the operator is securely guided to the most superficial and, thus, most accessible location of the foreign metal bodies or implants, so that the desired removal can be carried out easily by means of the necessary instruments. Accordingly, the operation for removing foreign metal bodies or implants can be carried out in a defined manner and within a substantially shorter time than in the past. Advantageously, the metal detecting device makes the metal body representation by means of an X-ray image converter superfluous. Consequently, long anesthesia periods are no longer necessary; in addition, the tissue is protected, so that an uncomplicated healing process is to be expected.

The foreign metal body is localized by directing the sensor pin which acts as a probe close to the suspected position. As soon as the top of the pin is exactly above the metal body being searched for, the field obstruction reaches a maximum. The measuring sensitivity of the metal detecting device is optimized by means of an automatic microprocessor-controlled unit. Preferably, the highly sensitive sensor circuit is connected to an A/D converter by means of a measuring amplifier, especially for indicating the received signals in the form of, for example, a bar-like LED display, an acoustic display or another graphic display or a direct reading instrument. Furthermore, the automatic setting to different sensitivities has the advantage that the input voltage applied to the field coil member does not have to be adjusted in dependence on the size of the foreign metal body.

Another advantage of the metal detecting device is the fact that the indicating device includes a maximum value memory and display which is operated simultaneously with an actual display. When using the aforementioned bar-like LED display, the maximum value is stored while there is a maximum deflection of the display and the maximum deflection is indicated continuously, so that, if the sensor pin is moved away from the closest position, the operator will be informed accordingly by the lowering of the actual display and the operator can trace the maximum point again. At the same time, an audible signal indicates that the maximum value has been found again. This also refers to other graphic representation possibilities, e.g., trailing indicators, maximum lines on a display and the like. Normally, the bar-like display will be integrated into the evaluation units connected to the sensor. However, in order to facilitate operation, it is also possible to integrate the indicator into the sensor pin, so that the operator can concentrate exclusively on the sensor pin and the observation of the display. Furthermore, as an alternative to a cable connection between the sensor pin and the evaluation equipment, it is also possible to provide an infrared transmission line which produces the advantage that the operator can work without interfering cable connections.

By using the metal detecting device of the present invention, it has become unnecessary to use complicated apparatuses, as they are required until now for carrying out X-rays, ultrasound examinations or computerized tomography. As a result of the novel design of the completely encased, temperature-resistant and, consequently, sterilizable sensor pin, the patient can be examined without difficulty by one operator directly in the three-dimensional space. The hand of the operator is guided in a defined manner to the location where the foreign metal body or the implant is located most superficially and is, therefore, most accessible, so that the desired removal can be realized by means of the necessary instruments. Consequently, the operation for removing foreign metal bodies or metal component implants can be made in a defined manner and within a substantially shorter time than in the past. The X-ray exposures of patients and personnel which had been inevitable in the past and long anesthesia times are no longer necessary. In addition, the tissue to be examined is protected considerably, so that a less complicated healing process can be expected. The operation is carried out only by the operator because the sensor pin of the metal detecting device is constructed for a single-handed operation. The assistant for operating an X-ray equipment is no longer necessary. Another advantage is the fact that, as a result of its construction, the sensor pin can also be directed around smallest parts of the body as well as those parts of the body which are usually difficult to reach for X-ray equipment. Especially the detection of implanted fixations, e.g. for auricle prosthesis, is simplified. Even the smallest size metal plates implanted into the viscerocranium can be found within a short period of time.

The foreign metal body is localized by directing the sensor pin which acts as a probe close to the suspected position. As soon as the central pin with the measuring coil member is exactly above the metal body searched for, the metal causes the field of construction to reach a maximum. An optimization of the measuring sensitivity of the metal detecting device is achieved by means of an automatic mechanism. Preferably, the measuring amplifier is connected to the measuring comparator by means of an A/D converter, especially for indicating the received digital signal of, for example, a bar-like LED display, an acoustic display or other graphic display or a direct reading instrument. Furthermore, the automatic setting to different sensitivities has the advantage that the input voltage applied to the field coil member does not have to be adjusted continuously in dependence on the size of the foreign metal body.

Another improvement of the metal detecting device is achieved by providing the indicating device with a maximum value display which can be operated simultaneously with an actual display. When using the aforementioned bar-like LED display, the maximum value is stored while there is a maximum deflection of the display and the deflection is indicated continuously so that, if the sensor pin is moved away from the closest position, the operator will be informed accordingly by the lowering of the actual display and the operator can trace the maximum point again. This is also true for other graphic representation possibilities, such as, trailing indicators, maximum lines on a display and the like.

The bar-like display is usually integrated into the evaluation unit connected to the sensor pin. However, to facilitate operation, it is also possible additionally to integrate the indicating device into the shaft of the sensor pin, so that the operator can concentrate on guiding the sensor pin and on the observation of the direct reading. In addition, as an alternative to a cable connection between the sensor pin and the evaluation, it is also possible to use an infrared transmission line, which has the advantage that the operator can work without interfering cable connections.

In order to improve the handling of the device, it is suggested to choose members which use a sensor coil wound on a ferrite core, wherein the sensor coil is preferably arranged inside a sensor head. In view of the fact that the coil is wound onto a ferrite core, the structural size of the measuring unit can be minimized because even small coils on a ferrite core produce a sufficiently large field. Moreover, the arrangement of the sensor coil in a sensor head serves to better determine the location outside of the human or animal body which is closest to the foreign body.

The following advantages result from the device according to the invention:

accurate, three-dimensional, quick localization of foreign metal bodies by means of visual displays, additional localization aid by means of an audible signal, single-handed operation of the device by one operator;

sensitivity control by the operator by means of a sensitivity sensor integrated into the measuring probe, simple and proved operation, optimized probes with different depths of penetration for surgical use in various fields, e.g., general surgery, ENT-surgery, dental surgery, oral surgery and facial surgery, unrestricted suitability for bone surgery operations, completely sterilizable: probes, connection cable, plugs are sterilizable in the autoclave together with the surgical instruments;

rugged, easily transportable device.

The various features of novelty which characterize the invention are pointed out with particularity in the claims annexed to and forming a part of this disclosure. For a better understanding of the invention, its operating advantages attained by its use, reference should be had to the drawing and descriptive matter in which there are illustrated and described preferred embodiments of the invention.

DESCRIPTION OF THE PREFERRED EMBODIMENT

Figure 1:
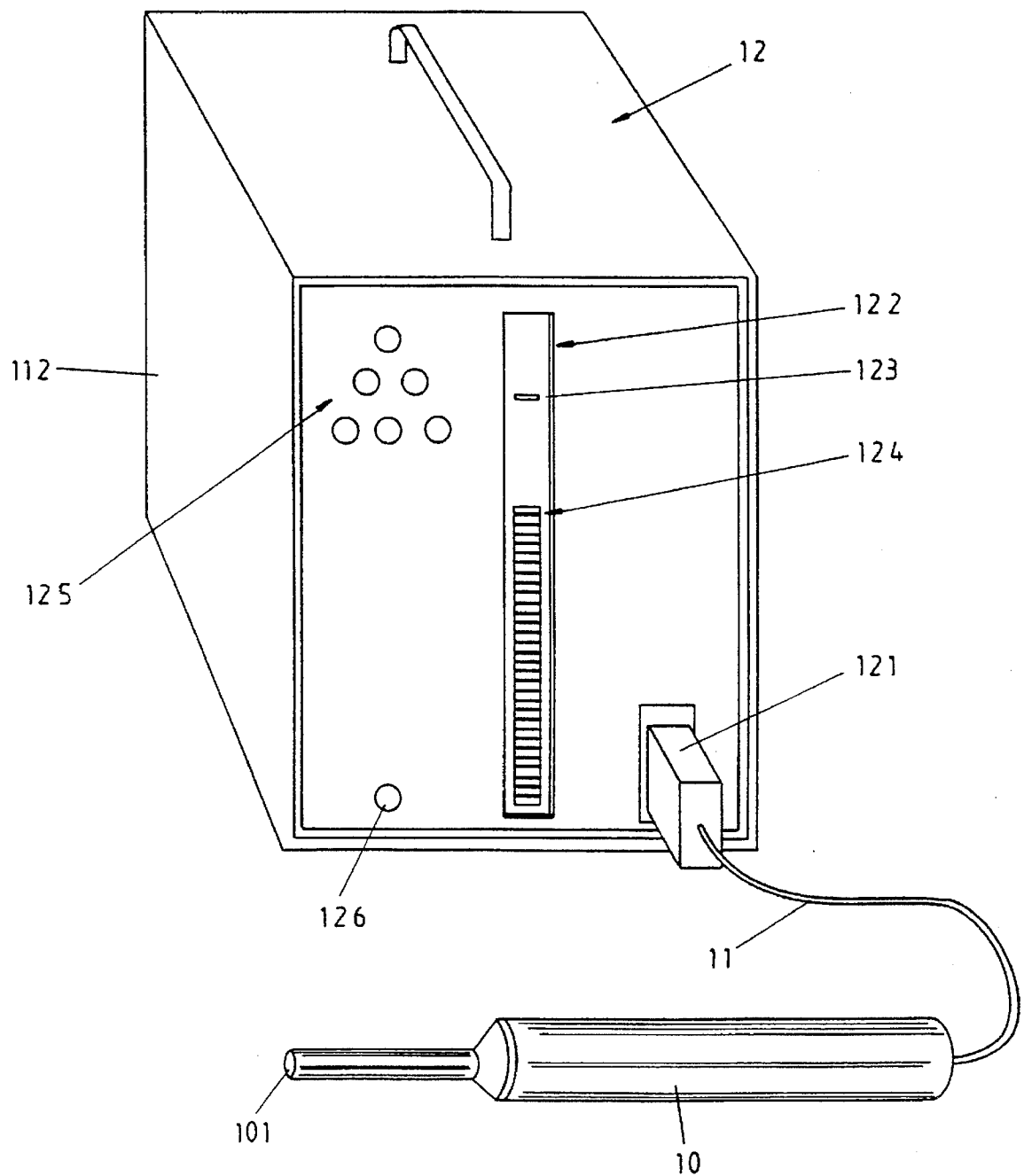
FIG. 1 is a perspective view of the metal detecting device according to the present invention.

As illustrated in FIG. 1 of the drawing, the metal detecting device according to the present invention is composed of a sensor which is preferably provided with a handle. The sensor head 101 which may be formed like a pin to permit insertion in subjacent regions. The sensor 10 is connected to an evaluation device 12 by means of a flexible line 11. Current is supplied by a power supply unit integrated into the housing 12 of the device. The evaluation device 12 uses a preferably detachable connection 121 for the flexible connection line 11 and, furthermore, a display unit 122 in the form of a bar-like display. The display is designed in such a way that it can simultaneously display a storable maximum display 123 as well as an actual display 124.

To achieve sensitivity, an automatic microprocessor unit is provided. After an adjustable time interval, the trailing indicator of the bar-like display is reset to zero. The same is true for any other graphic display switch which may be provided. The graphic display can be supported by an acoustic device which changes the tone pitch thereof. In that case, the evaluation device is arranged inside the sensor pin 10.

Figure 3:
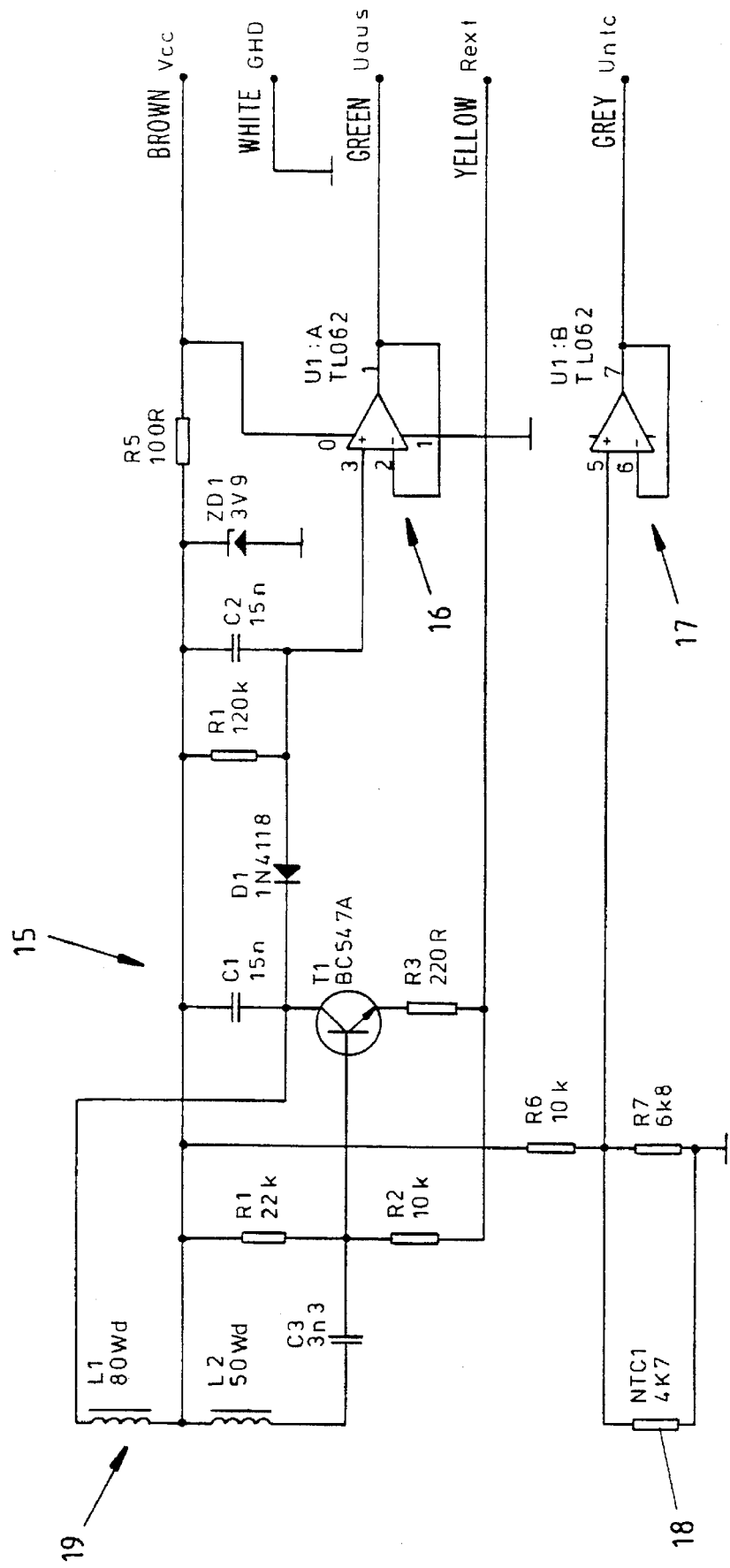
FIG. 3 is a diagram showing the circuit for the sensor field coil.

Instead of the cable connection 11 between the evaluation device 12 and sensor pin 10, it is also possible to provide an infrared line which makes an interfering cable connection superfluous. Additionally provided may be, for example, a changeover switch for adjusting the sensitivity, wherein the switch may be also a multiple circuit breaker. Reference number 126 denotes a reset unit for resetting the device to zero before making a new measurement. In another embodiment, the shaft of the sensor 10 may include the bar-like display 122. In that case, the coil members 19 (L1, L2) are arranged in the sensor head, as is clear from FIG. 3.

Figure 2:
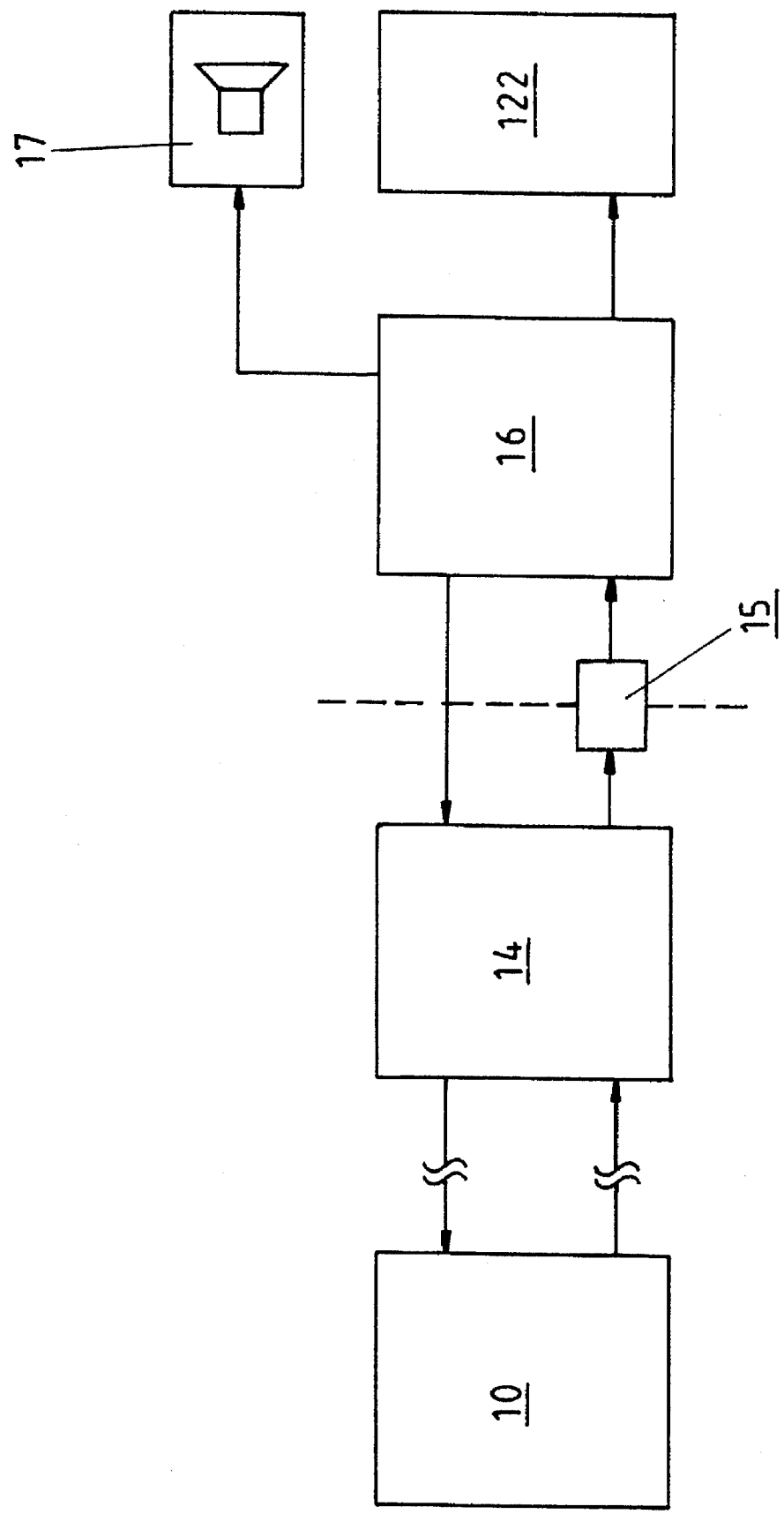
FIG. 2 is a block diagram of the device.

According to the diagram shown in FIG. 2, the sensor 10 is connected to a measuring amplifier 14, wherein the components 10 and 14 represent the analogous circuit elements. The measuring amplifier 14 delivers measuring signals to a comparator 16 via an A/D converter. The comparator forms part of the evaluation unit. The measurement results are displayed on a bar-like display which utilizes a peak holding system. Additionally provided may be an audible signal transmitter 17 which responds when the sensor 10 is at a minimum distance from the foreign metal body in the human or animal body tissue.

The components required for the circuit are known in the art. Thus, the measurement signals received by the sensor coil which is wound onto a ferrite core are picked up by a transistor T1 via an amplifier 15. The signals are processed by operation amplifiers 16 and 17 which are stabilized feed-back amplifiers and ensue a high-current amplification. A hot-temperature conductor (NTC1) denoted by reference number 18 is arranged approximately in the center of the ferrite core onto which the sensor coil (L1,L2) is wound.

The sensor 10 is preferably shaped like a pencil or ballpoint pen and includes a sensor head 101 having a small point-like surface of about 3.5 mm. Further automation is achieved by integrating the evaluation device 12 in the sensor 10.

The present invention also relates to a method of localizing a foreign metal body which has penetrated or has been implanted into a human or animal body by guiding the above-described metal detecting device in three-dimensional space single-handedly around the the parts of the body containing the foreign metal body.

The diodes 125 shown in FIG. 1 are connected successively one behind the other to make it possible to differentiate between several objects. The device is returned into the initial position after a localization and measurement has been carried out by placing a blow against the sensor head or pin 101.

I claim:

1. A metal detecting device for localizing a foreign metal body which has penetrated or been implanted in a human or animal body, the metal detecting device comprising a measuring amplifier for producing output signals, a sensor connected to the measuring amplifier, a coil member mounted in the sensor, and a measuring comparator for evaluating the output signals of the measuring amplifier as a measure of a field influence caused by the foreign metal body, wherein said measuring comparator comprises an indicating device, and wherein the indicating device comprises a maximum value memory and display, further comprising an actual display simultaneously operated with the maximum value memory and display.

2. The metal detecting device according to claim 1, comprising a power supply unit for delivering a high-frequency voltage, wherein the sensor is connected to the supply unit.

3. The metal detecting device according to claim 2, wherein the frequency of the power supply unit is between 500 and 600 kHz.

4. The metal detecting device according to claim 1, wherein the measuring comparator comprises a change-over switch for adjusting different measuring sensitivities of the measuring comparator.

5. The metal detecting device according to claim 1, comprising an A/D converter connecting the measuring amplifier to the measuring comparator.

6. The metal detecting device according to claim 1, wherein the indicating device is one of a bar-like LED-display, a bar chart display and an audible display.

7. The metal detecting device according to claim 4, further comprising an automatic microprossor-controlled unit for controlling the sensitivity.

8. The metal detecting device according to claim 1, comprising an evaluation device and a flexible cable connecting the sensor to the evaluation device.

9. The metal detecting device according to claim 1, comprising an evaluation device and an infrared transmission line connecting the sensor to the evaluation device.

10. The metal detecting device according to claim 1, wherein the sensor comprises a handle, the indicating device being integrated into the handle of the sensor.

11. The metal detecting device according to claim 1, wherein the sensor comprises a handle, an evaluation device being integrated into the handle of the sensor.

12. The metal detecting device according to claim 1, wherein the coil member comprises a ferrite core and a sensor coil wound onto the ferrite core, the sensor comprising a pin-shaped sensor head, the sensor coil being mounted in the sensor head.

* * * * *